United States Patent [19]

Emenaker et al.

[11] Patent Number: 5,569,231
[45] Date of Patent: Oct. 29, 1996

[54] TRISECTION SANITARY NAPKIN

[75] Inventors: Ralph R. Emenaker, Hamilton; Charles W. Amos, Jr., Cincinnati, both of Ohio

[73] Assignee: The Procter & Gamble Company, Cincinnati, Ohio

[21] Appl. No.: 514,165

[22] Filed: Aug. 11, 1995

Related U.S. Application Data

[63] Continuation of Ser. No. 339,511, Nov. 14, 1994, Pat. No. 5,460,623, which is a continuation of Ser. No. 204,821, Mar. 1, 1994, abandoned.

[51] Int. Cl.⁶ .......................... A61F 13/15; A61F 13/20
[52] U.S. Cl. ........................... 604/385.1; 604/358
[58] Field of Search .................... 604/358, 368, 604/372, 378, 385.1

[56] References Cited

U.S. PATENT DOCUMENTS

| | | |
|---|---|---|
| 3,343,543 | 9/1967 | Glassman . |
| 3,575,174 | 4/1971 | Mogor . |
| 3,874,385 | 4/1975 | Gellert . |
| 3,954,107 | 5/1976 | Chesky et al. . |
| 3,965,906 | 6/1976 | Karami . |
| 4,029,101 | 6/1977 | Chesky et al. . |
| 4,059,114 | 11/1977 | Richards . |
| 4,062,362 | 12/1977 | Schaar . |
| 4,212,302 | 7/1980 | Karami . |
| 4,217,901 | 8/1980 | Bradstreet et al. . |
| 4,551,191 | 11/1985 | Kock et al. . |
| 4,560,372 | 12/1985 | Pieniak . |
| 4,578,068 | 3/1986 | Kramer et al. . |
| 4,578,070 | 3/1986 | Holtman . |
| 4,600,458 | 7/1986 | Kramer et al. . |
| 4,605,402 | 8/1986 | Iskra . |
| 4,655,759 | 4/1987 | Romans-Hess et al. . |
| 4,731,071 | 3/1988 | Pignuel . |
| 4,795,455 | 1/1989 | Luceri et al. . |
| 4,840,692 | 6/1989 | Kamstrup-Larsen . |
| 4,917,929 | 4/1990 | Heinecke . |
| 4,950,264 | 8/1990 | Osborn, III . |
| 4,973,325 | 11/1990 | Sherrod et al. . |
| 4,988,345 | 1/1991 | Reising . |
| 5,009,651 | 4/1991 | Kamishioiri et al. . |
| 5,009,653 | 4/1991 | Osborn, III . |
| 5,028,224 | 7/1991 | Pieper et al. . |
| 5,171,302 | 12/1992 | Buell . |
| 5,176,668 | 1/1993 | Bernardin . |
| 5,197,959 | 3/1993 | Buell . |
| 5,248,309 | 9/1993 | Serbiak et al. ............... 604/368 |
| 5,366,451 | 11/1994 | Levesque . |
| 5,401,267 | 3/1995 | Couture-Dorschner et al. . |

FOREIGN PATENT DOCUMENTS

| | | |
|---|---|---|
| 0136524A1 | 8/1984 | European Pat. Off. . |
| 0162451A1 | 5/1985 | European Pat. Off. . |
| 0335253A1 | 3/1989 | European Pat. Off. . |
| 0336578 | 10/1989 | European Pat. Off. ............... 604/368 |
| 2554714 | 5/1985 | France . |
| 5244155 | 11/1977 | Japan ..................... 604/368 |
| 2124499 | 2/1984 | United Kingdom . |
| WO91/09579 | 12/1990 | WIPO . |
| WO92/07535 | 10/1991 | WIPO . |
| WO94/02092 | 2/1994 | WIPO . |

*Primary Examiner*—John G. Weiss
*Assistant Examiner*—P. Zuttarelli
*Attorney, Agent, or Firm*—Larry L. Huston; E. Kelly Linman; Jacobus C. Rasser

[57] ABSTRACT

A sanitary napkin having an absorbent core with three longitudinally oriented trisections, a central trisection flanked by two outboard trisections. The absorbent core is formed of a single layer of tissue. The single layer of tissue is folded on itself to provide a two-ply thickness at each of the outboard trisections and a single thickness at the central trisection. The two plies of the outboard trisections are preferably adhered together. Absorbent gelling materials are disposed in each of the outboard trisections. The central trisection is substantially free of absorbent gelling materials. The sanitary napkin also preferably comprises a secondary topsheet intermediate the topsheet and the absorbent core. The secondary topsheet is also substantially free of absorbent gelling materials.

8 Claims, 2 Drawing Sheets

TRISECTION SANITARY NAPKIN

This is a continuation of application Ser. No. 08/339,511, filed on Nov. 14, 1994, now U.S. Pat. No. 5,460,623 which is a continuation of application Ser. No. 08/204,821, filed on Mar. 1, 1994, now abandoned.

FIELD OF THE INVENTION

The present invention relates to sanitary napkins, particularly to sanitary napkins which deform to comfortably fit against and reliably intercept menses from the wearer.

BACKGROUND OF THE INVENTION

Sanitary napkins are well known in the art. Sanitary napkins intercept menses upon discharge, and thereby protect the clothing and bedding of the wearer from soiling by the menses.

However, sanitary napkins can and do bunch and rope during use. This occurrence reduces the target area of the sanitary napkin, allowing discharged menses to soil the undergarment of the wearer and causing wearer discomfort.

One attempt to deal with this problem is to provide the sanitary napkin with a means for resisting deformation under the action of the wearer's body movements. Such resistance to deformation is accomplished by providing a sanitary napkin having crush resistance. Crush resistance is related to the ability of the napkin to resist crushing forces applied to the longitudinal side edges of the napkin during use, in order to reduce unintended bending, twisting, and folding of the napkin. By making the sanitary napkin crush resistant, allegedly the sanitary napkin does not bunch or rope during use. A sanitary napkin alleging to have such crush resistance is taught in U.S. Pat. No. 4,217,901 issued Aug. 19, 1980 to Bradstreet et al.

An improvement to this approach is to provide a sanitary napkin having both high flexibility and high capacity. Preferably such a sanitary napkin is thin, and closely conforms to the anatomy of the wearer. A thin, high flexibility, high capacity sanitary napkin provides the best of all worlds. A relatively thin napkin has less in use wearer awareness. A high flexibility napkin provides greater wearer comfort, without being obtrusive under tight clothing. A high capacity napkin can be worn during all days of the menstrual cycle.

Such a high flexibility, high capacity sanitary napkin conforms to and moves with the wearer, rather than resisting the actions and forces imposed by the wearer as taught by the aforementioned U.S. Pat. No. 4,217,901 issued to Bradstreet et al. This arrangement provides the advantage of greater wearer comfort without an unintentional reduction in the target area. Such a sanitary napkin has met with great commercial success in recent years, and is made according to commonly assigned U.S. Pat. No. 4,950,264 issued Aug. 21, 1990 to Osborn, Ill. and commonly assigned U.S. Pat. No. 5,009,653 issued Apr. 23, 1991 to Osborn, III. The foregoing U.S. Pat. Nos. 4,950,264 and 5,009,653 are incorporated herein by reference.

However, there remains a need for a thin, high flexibility, high capacity sanitary napkin which is even less crush resistant than those made according to U.S. Pat. Nos. 4,950,264 and 5,009,653. Such a sanitary napkin must not provide unintended or uncomfortable resistance to lateral compression from the thighs of the wearer, and yet still conform to the anatomy of the wearer. One manner in which this may be accomplished is by longitudinally weakening the sanitary napkin so that a line of weakness, such as a hinge line, results.

One such attempt in the art provides a longitudinally articulated sanitary napkin as found in U.S. Pat. No. 3,954,107 issued May 4, 1976 to Chesky et al. However, the Chesky et al. sanitary napkin does not have a generally planar topsheet. The topsheet is interrupted by a channel having the shape of an inverted T. This arrangement requires the sanitary napkin to have more thickness than is necessary, and thereby provides an unduly high degree of wearer awareness.

Other attempts have been made in the art to provide longitudinal grooves in a sanitary napkin. For example, U.S. Pat. No. 4,795,455 issued Jan. 3, 1989 to Luceri et al. discloses a napkin pad liner having a longitudinal channel embossed along nearly the entire length of the liner. This arrangement provides a high density region in the center, allegedly improving longitudinal fluid distribution. However, this arrangement has the drawback that fluid may not properly laterally wick into the storage areas laterally outboard of the channel.

Other embodiments of Luceri et al. show opposed channels, one on either face of the napkin pad liner. This arrangement provides the disadvantage that the sanitary napkin is predisposed to bend either concave up or concave down, causing a less predictable performance.

In a similar attempt, U.S. Pat. No. 4,059,114 issued Nov. 22, 1977 to Richards discloses an absorbent pad having embossments in the web. This arrangement again, has the embossments in the top surface of the napkin and relies upon the fluid handling characteristics noted above. Moreover, a channel embossed in the top of the sanitary napkin predisposes it to bend in a concave upward configuration, rather than a preferred convex upward configuration. A similar attempt is found in U.S. Pat. No. 4,655,759 issued Apr. 7, 1987 to Romans-Hess et al. which discloses a sanitary napkin having embossed channels adjacent the longitudinal side edges to minimize side staining to eliminate leakage and allow the sides of the napkin to told upwards during use.

Yet other attempts in the art to provide longitudinal lines of weakness in the top surface of the sanitary napkin include U.S. Pat. Nos. 3,343,543 issued Sept. 26, 1967 to Glassman; 3,575,174 issued Apr. 20, 1971 to Mogor; and 4,840,692 issued Jun. 20, 1989 to Kamstrup-Larsen. However, these arrangements all disclose multiple lines of weakness and/or relatively thick napkins. Multiple lines of weakness may not require the sanitary napkin to buckle along the center. Relatively thick napkins suffer from the disadvantages noted above.

Yet another attempt in the art to provide a sanitary napkin which is longitudinally weakened is disclosed in commonly assigned U.S. Pat. Nos. 5,171,302 issued Dec. 15, 1992 to Buell and 5,197,959 issued Mar. 30, 1993 to Buell. These references disclose a sanitary napkin having a flexure resistant deformation element which provides the sanitary napkin with a convex upward configuration when worn. This configuration is maintained due to the lateral pressure from the wearer's thighs.

Yet other attempts in the art have been made to not rely upon longitudinal embossed channels to improve fluid distribution. For example, U.S. Pat. No. 4,212,302 issued Jul. 15, 1980 to Karami, discloses an absorbent article having hydrocolloid material in the side margins and end margins, spaced from the fluid receiving region of the pad. The fluid receiving region is in the central portion of the pad and is substantially free of the hydrocolloid materials. However, this arrangement suffers from the difficulties associated with having both longitudinal and transverse hydrocolloid distributions necessary to provide the central region free of hydrocolloid material. Compounding this problem Karami requires an additional manufacturing step, i.e., that the surface against which the hydrocolloid materials are to be placed is first wetted. Even with this additional manufacturing step, if the Karami hydrocolloid material is near the topsheet of the absorbent article, there is a risk of the hydrocolloid material contacting the skin of the wearer.

Accordingly, it is an object of this invention to provide a sanitary napkin which does not rely upon crush resistance to maintain the target area. It is further an object of this invention to provide a sanitary napkin having differential flexibility, so that lateral hinging occurs in lieu of lateral crush resistance. It is further an object of this invention to provide a sanitary napkin which does not rely upon embossed lines for adequate fluid handling characteristics.

SUMMARY OF THE INVENTION

The invention comprises an absorbent core. The absorbent core has orthogonal longitudinal and lateral centerlines. The absorbent core comprises three longitudinally oriented trisections, a central trisection having a first thickness and being laterally flanked on each side by an outboard trisection. The outboard trisections have a second thickness. The first thickness of the central trisection is less than the second thickness of the outboard trisections. Absorbent gelling material is disposed in each of the outboard trisections while the central trisection is substantially free of absorbent gelling material. When the core is subjected to lateral pressure it buckles at the central trisection.

The absorbent core may comprise a single sheet of tissue, preferably airlaid tissue. The absorbent core has longitudinal side edges which may be folded back, so that when the absorbent core is folded back upon itself at the longitudinal side edges, a two-ply thickness is formed at and defining the outboard trisections while a single ply thickness defining the central trisection and a gap is formed between the longitudinal side edges of the tissue.

Absorbent gelling materials are disposed in each of the outboard trisections, while the central trisection is substantially free of absorbent gelling materials. Preferably the absorbent gelling materials are held in place by adhesive. The adhesive stiffens the outboard trisections of the core, so that when the core is subjected to laterally applied pressures, it will buckle at the central trisection.

The core is particularly suitable for use in a sanitary napkin. When worn, the core, and hence the entire sanitary napkin, will buckle along the central trisection and assume a convex upward configuration.

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad. A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal and other discharges from the wearer's body (e.g., blood, menses, and urine). Interlabial devices which reside partially within and partially external of the wearer's vestibule are also within the scope of this invention. It should be understood, however, that the present invention is also applicable to other feminine hygiene or catamenial pads such as panty liners, or other absorbent articles such as incontinence pads, and the like.

Figure 1:
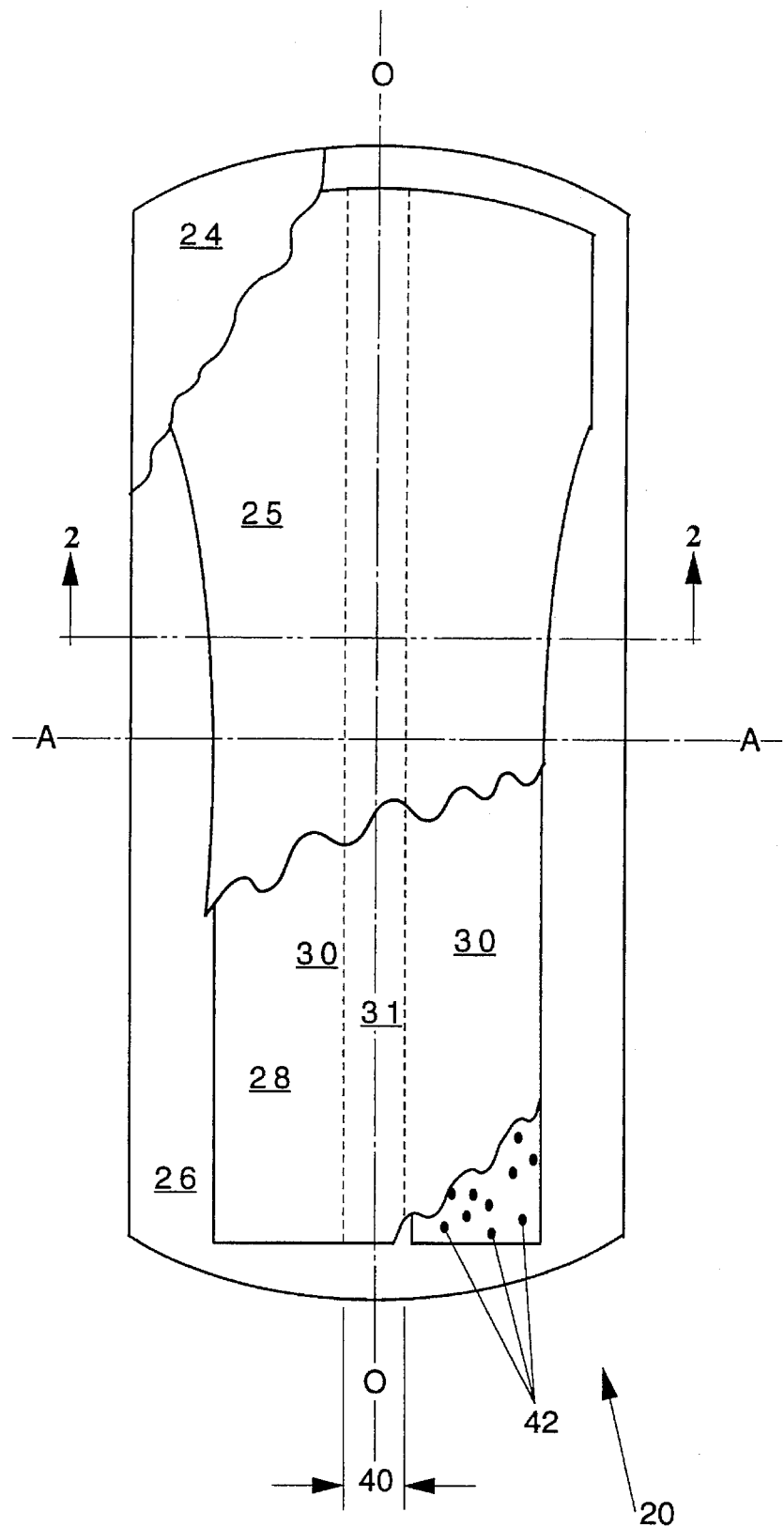
FIG. 1 is a top plan view, shown partially in cutaway, of a sanitary napkin according to the present invention.

FIG. 1 is a top plan view of the sanitary napkin 20 of the present invention in a flat state with portions of the structure being cut-away to more clearly show the construction of the sanitary napkin 20 and with the portion of the sanitary napkin 20 which faces or contacts the wearer, oriented towards the viewer. As shown in FIG. 1, the sanitary napkin 20 preferably comprises a liquid pervious topsheet 24, a liquid impervious backsheet 26 joined to the topsheet 24, and an absorbent core 28 positioned between the topsheet 24 and the backsheet 26. The absorbent core 28 has two major faces, a first major face oriented towards the topsheet 24 and a second major face oriented towards the backsheet 26. Preferably the sanitary napkin 20 according to the present invention further comprises an optional secondary topsheet 25. The secondary topsheet 25 is preferably disposed between the absorbent core 28 and the topsheet 24.

The sanitary napkin 20 has two centerlines, a longitudinal centerline O—O and a lateral centerline A—A. The term "longitudinal" as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 and is generally perpendicular to the longitudinal direction. The Z-direction is orthogonal both the longitudinal and lateral centerlines of the sanitary napkin 20 and extends outwardly from the plane of the sanitary napkin 20, which is defined by the longitudinal centerline O—O and the lateral centerline A—A.

The long edges of the sanitary napkin 20, which are align with the longitudinal centerline O—O, are the longitudinal side margins of the sanitary napkin 20. The ends of the sanitary napkin 20 joining the longitudinal side margins are the transverse ends of the sanitary napkin 20. Collectively the longitudinal side margins and transverse ends of the sanitary napkin 20 define its periphery.

While the topsheet 24, the backsheet 26, and the absorbent core 28 may be assembled in a variety of well known configurations (including so called "tube" products or side flap products), preferred sanitary napkin configurations are described generally in U.S. Pat. No. 4,950,264, "Thin, Flexible Sanitary Napkin" issued to Osborn on Aug. 21, 1990; U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; U.S. Pat. No. 4,589,876, "Shaped Sanitary Napkin With Flaps" issued to Van Tilburg on Aug. 18, 1987. Each of these patents is hereby incorporated herein by reference. FIG. 1 shows a preferred embodiment of the sanitary napkin 20 in which the topsheet 24 and the backsheet 26 have length and width dimensions generally larger than those of the absorbent core 28. The topsheet 24 and the backsheet 26 extend beyond the edges of the absorbent core 28 to thereby form not only portions of the periphery, but also side flaps (not shown) if so desired.

The absorbent core 28 may be any absorbent means capable of absorbing or retaining liquids (e.g., menses and/or urine). The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins, such as tissue, particularly air-laid tissue. Examples of other suitable absorbent materials include comminuted wood pulp generally referred to as airfelt, creped cellulose wadding; meltblown polymers including coform; chemically stiffened, modified or cross-linked cellulosic fibers; synthetic fibers such as crimped polyester or polyolefin fibers; peat moss; absorbent foams; absorbent sponges; superabsorbent polymers; absorbent gelling materials 42; or any equivalent material or combinations of such materials.

The configuration and construction of the absorbent core 28 may also be varied (e.g., the absorbent core 28 may have varying caliper zones (e.g., profiled so as to be thicker or thinner in the center), hydrophilic gradients, superabsorbent gradients, or lower density and lower average basis weight acquisition zones; or may comprise one or more layers or structures). The total absorbent capacity of the absorbent core 28 should, however, be compatible with the design loading and the intended use of the sanitary napkin 20. Further, the size and absorbent capacity of the absorbent core 28 may be varied to accommodate different uses such as incontinence pads, panty liners, regular sanitary napkins, or overnight sanitary napkins.

Figure 2:
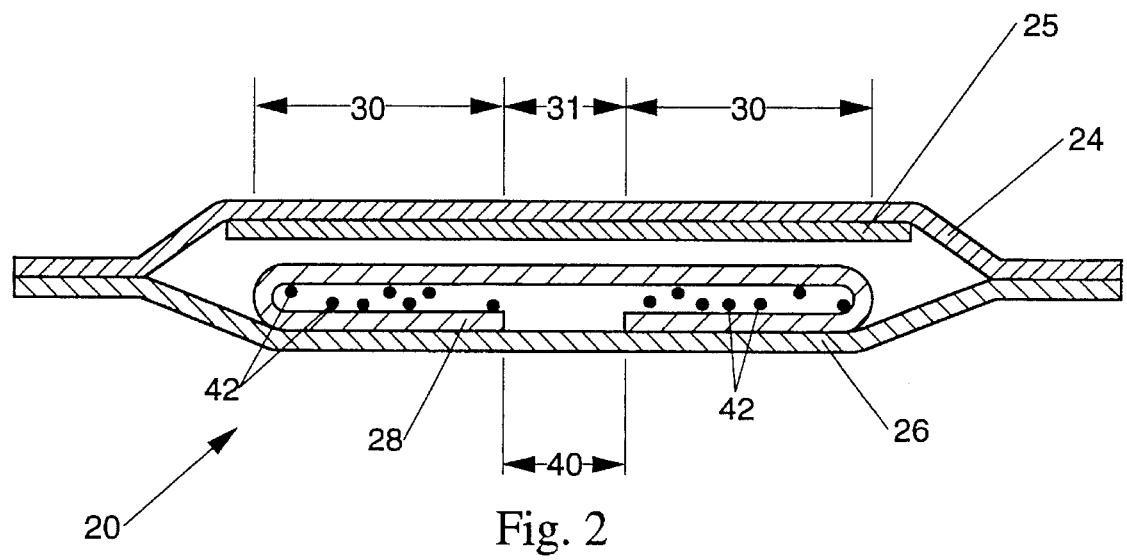
FIG. 2 is a vertical sectional view taken along line 2—2 of FIG. 1 having no cutaway and showing the core and secondary topsheet in spaced apart positions for clarity.

Referring to FIG. 2, the absorbent core 28 comprises three trisections, a central trisection 31 flanked by two outboard trisections 30. The central trisection 31 preferably lies along and is symmetric about the longitudinal centerline O—O. The outboard trisections 30 are juxtaposed with the central trisection 31 and may form the longitudinal side edges of the absorbent core 28. The central trisection 31 is preferably flexible relative to the outboard trisections 30, so that the sanitary napkin 20 can deform at or throughout the central trisection 31 in response to lateral pressure from the wearer's thighs prior to encountering substantial deformation of the outboard trisections 30.

Preferably the absorbent core 28 comprises an airlaid tissue, C-folded to have a dual ply thickness in the outboard trisections 30 and a single ply thickness along the central trisection 31. The outboard trisections 30 are preferably symmetrically disposed about the longitudinal centerline O—O and are equal in size. The central trisection 31 and outboard trisections 30 need not be equal in width, however. The central trisection 31 may have a lesser width than the outboard trisections 30, to ensure sufficient capacity as described below. Also, if the central trisection 31 is narrower in width than the outboard trisections 30, the sanitary napkin 20 more readily conforms to the anatomy of the wearer. Furthermore, a narrower central trisection 31 provides the core 28 with greater capacity, and hence greater protection upon heavy loadings.

For a sanitary napkin 20 according to the present invention the core may have a width of 50 to 70 millimeters. The central trisection 31 may range from 0 to 30 millimeters in width, and preferably from 5 to 12 millimeters in width, while each outboard trisection 30 may measure from 13 to 35 millimeters in width. Alternatively, the edges of the outboard trisections 30 may abut, may be spaced as close as 3 millimeters apart, or for the embodiments described herein, may preferably be spaced apart in a gap 40 of 5 to 12 millimeters, as described above. The gap 40 defines the central trisection 31.

The edges of the outboard trisections 30 may be straight and parallel to the longitudinal centerline O—O as shown, or may be arcuate. Arcuate edges can either be concave towards or convex outwards from the longitudinal centerline O—O. If this configuration is selected, the absorbent gelling materials 42 should be limited to the narrowest width of the outboard trisections 30, so that the likelihood of the absorbent gelling materials 42 becoming free and contacting the skin of the wearer is minimized. Alternatively, the edges may monotonically taper towards either transverse end of the sanitary napkin 20.

Preferably, the gap 40 is oriented towards the backsheet 26. This allows the face of the core 28 oriented towards the topsheet 24 to be generally planar.

The sides of the core may be straight, or may be arcuate in a configuration concave outward from the longitudinal centerline O—O. If an hourglass shaped core 28 having arcuate longitudinal side edges is selected, the core width should be measured at the narrowest point.

The absorbent core 28 may preferably further comprise absorbent gelling materials 42 as are well known in the art. Preferably the central trisection 31 is substantially free of absorbent gelling materials 42, in order to enhance fluid distribution in the longitudinal direction. Also, the potential hazard associated with absorbent gelling materials 42 directly contacting the skin are reduced if the central trisection 31 is substantially free of absorbent gelling materials 42. This potential hazard is possible, although unlikely, because the single ply thickness of the central trisection 31 may not allow adequate insulation of the absorbent gelling materials 42 from the pervious topsheet 24. Also, it may be difficult to adhere absorbent gelling materials 42 to the single ply thickness of the central trisection 31 in a conventional manufacturing process. If the edges of the outboard trisections 30 abut, the absorbent gelling materials. 42 may be distributed throughout the entire width of the core 28, including the central trisection 31.

The outboard trisections 30 preferably have a double thickness as noted above. More preferably, the outboard trisections 30 are formed by folding the tissue of the absorbent core 28 over upon itself at the longitudinal side edges of the absorbent core 28. By having the material forming the outboard trisections 30 of the absorbent core 28 folded over at the longitudinal edges, the chances of absorbent gelling materials 42 escaping from the outboard trisections 30 in the laterally outward directions are minimized. Should absorbent gelling materials 42 become dislodged and move laterally inward, they will still be restrained from migrating towards the skin by adhesive or by the single thickness of the central trisection 31 described above.

The absorbent gelling materials 42 contained in the outboard trisections 30 are preferably held in place by adhesive. The adhesive may be applied as an overall spray, printed as micropatterns, sprayed in overlapping or nonoverlapping spiral loops, or sprayed in a random meltblown pattern. Overlapping spiral loops are generally preferred because such an arrangement prevents the outboard trisections 30 from becoming too stiff and allows good manufacturing control, preventing adhesive from occurring in the central trisection 31.

The adhesive in the outboard trisections 30 serves three purposes. First, the adhesive joins together the two plies of the tissue forming the outboard trisections 30, to make a laminate construction. This laminate construction has the effect of stiffening the outboard trisections 30 relative to the central trisection 31. The stiffening occurs because more plies of tissue are present and because the adhesive has more stiffness than the tissue. By combining additional plies and the stiffness of the adhesive, the central trisection 31 will be relatively flexible relative to the outboard trisection 30. This arrangement has the advantage of allowing the sanitary napkin to more comfortably conform to the shape of the wearer while providing adequate capacity for all of the menstrual cycle.

Second, while the outboard trisections 30 are relatively stiff in comparison to the central trisection 31, the overall construction of the sanitary napkin must not be too stiff—so that wearer discomfort is avoided. Sanitary napkins having a relatively stiff overall construction were known and used in the prior art. However, with the commercially successful high capacity, high flexibility sanitary napkins available today, the consumer has come to expect a sanitary napkin which is both flexible in its overall construction and which conforms to the body of the wearer.

If a pressure sensitive hot melt adhesive is used to join the two plies of the outboard trisection 30, and if the AGM is placed in direct contact with the hot melt adhesive, the teachings of the prior art crush resistant napkin constructions can be avoided. Particularly, the aforementioned U.S. Pat. No. 4,217,901 issued to Bradstreet et al. teaches applying the heat on the side of the core 28 which is opposite the absorbent gelling materials 42. The Bradstreet et al. arrangement allegedly causes the migration of moisture, thereby forming a relatively crush resistant sanitary napkin. In order to avoid the crush resistant sanitary napkin of Bradstreet et al., the heat source found in a hot melt adhesive and absorbent gelling material must be placed together, so that the moisture migration and bond formation disclosed therein does not occur.

Third, the adhesive helps to entrap and join the absorbent gelling material particles to and within the absorbent core 28. This arrangement minimizes the safety concerns of avoiding direct contact of the absorbent gelling materials 42 with the skin of the wearer.

Figure 3:
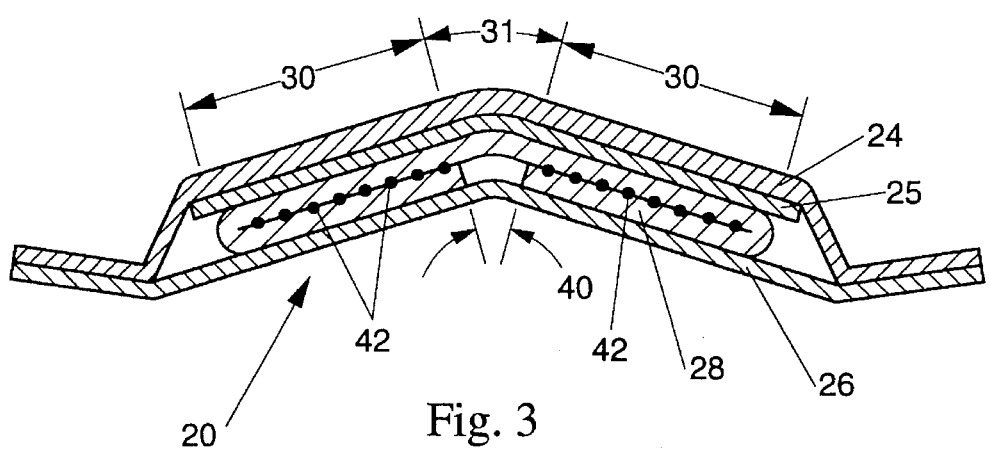
FIG. 3 is the sanitary napkin of FIG. 2 while in use and showing the resulting conformation to the anatomy of the wearer, as the absorbent core buckles at the central trisection.

Referring to FIG. 3, preferably the outboard trisections 30 are folded so that the first major surface of the sanitary napkin 20 which is oriented towards the topsheet 24 is generally planar, and the relieved portion of the absorbent core 28 formed by the single ply thickness of the central trisection 31 is oriented towards the backsheet 26. This arrangement provides the advantage that the sanitary napkin has a more uniform and aesthetically pleasing appearance to the user when viewed from and through the pervious topsheet 24 (assuming a secondary topsheet 25 is not included), and, more importantly, is predisposed to a convex upward configuration, and possible a W-shaped cross section during use. Furthermore, this arrangement potentially provides a barrier between any loose particles of absorbent gelling material 42 and the pervious topsheet 24.

To assist in predisposing the sanitary napkin 20 to a convex upward configuration during use, the absorbent core 28 may be joined to the backsheet 26. Preferably, longitudinally oriented lines of adhesive join the outboard trisections 30 of the absorbent core 28 to the backsheet 26. In this manner, the central trisection 31 can freely float independent of the backsheet 26 and is thereby decoupled from the backsheet 26 to a limited extent. Preferably the adhesive which attaches the outboard trisections 30 of the absorbent core 28 to the backsheet 26 has a width ranging from 1 to 20 millimeters, so that such adhesive is not as wide as the outboard trisection 30 which it joins to the backsheet 26. It is desirable that such adhesive allow the sanitary napkin to form a W formation, and not impart excessive stiffness to the sanitary napkin.

The absorbent core 28 is preferably made of tissue and more preferably an airlaid tissue. An airlaid tissue is preferred over a wetlaid tissue because of its greater wet strength which avoids wet collapse and intrinsically higher void volume. The tissue should have properties which make it suitable for use in the sanitary napkin 20 according to the present invention. In particular, a tissue having a wet tensile strength of at least 100 grams per centimeter as determined by ASTM Standard D829-49 is preferred, so that the tissue recovers from lateral compression after being wetted by menses.

The tissue may be embossed to provide strength. The tissue may have a basis weight of 30 to 41 pounds per 3,000 square feet. A highly suitable tissue is available from the Fort Howard Company of Green Bay, Wisc. as grade 817.

Referring back to FIG. 1, preferably the sanitary napkin 20 is also provided with a secondary topsheet 25 as noted above. The secondary topsheet 25 may be made of a tissue material identical to that used for the absorbent core 28. This provides convenience in manufacturing. If desired, the secondary topsheet 25 may have a hydrophilicity and density lesser than those of the absorbent core 28, so that inimical fluid handling properties do not result.

The secondary topsheet 25 is preferably a single ply so that it does not add undue or unnecessary thickness to the sanitary napkin. The secondary topsheet 25 may be dogbone shaped, to provide an aesthetically pleasing appearance to the user. This arrangement also provides the advantage that as the wearer's thighs laterally compress the sanitary napkin 20 according to the present invention, any portions of the secondary topsheet 25 which lie laterally outboard of the absorbent core 28 are first contacted by the thighs of the wearer and can deform in response to the lateral pressures exerted thereby. This arrangement provides the advantage that the sanitary napkin 20 will have a lesser apparent crush resistance during use.

Preferably the secondary topsheet 25 does not contain absorbent gelling materials 42 so that any potential occurrences of gel blocking are minimized and fluid handling properties are not compromised. Even without the addition of absorbent gelling materials 42, the secondary topsheet 25 beneficially adds to the overall absorbent capacity of the sanitary napkin 20.

If desired, the secondary topsheet 25 may be adhered to the topsheet 24 using spiral adhesive, meltblown adhesive, or an overall spray. An overall spray is preferred because this arrangement provides intimate contact between the secondary topsheet 25 and the topsheet 24, and promotes wicking of fluids therebetween. It is important, however, that the porosity of the topsheet 24 not be inimically affected by or blocked by this adhesive.

Adhering the secondary topsheet 25 to the topsheet 24 provides the advantage that the secondary topsheet 25 and absorbent core 28 do not become laminated together. Instead both the secondary topsheet 25 and the core 28 are joined to the outwardly facing component, i.e., the topsheet 24 and backsheet 26, respectively.

The backsheet 26 is impervious to liquids and is preferably manufactured from a thin plastic film, although other flexible liquid impervious materials may also be used. As used herein, the term "flexible" refers to materials which are compliant and will readily conform to the general shape and contours of the human body. The backsheet 26 prevents exudates absorbed and contained in the absorbent core 28 from wetting the clothing and bedding of the wearer. The backsheet 26 may alternatively comprise a film-coated nonwoven material. Preferably, the backsheet 26 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P-18-1401, and by Tredegar Corporation, of Richmond, Va., under the designation X8297.

The backsheet 26 has an inwardly oriented surface oriented towards the absorbent core 28 and an outwardly oriented surface opposed thereto. The outwardly oriented surface of the backsheet 26 faces, and in use contacts, the undergarment of the wearer. If desired, strips of adhesive 34 may be joined to the outwardly facing surface of the backsheet 26 to facilitate attachment of the sanitary napkin 20 to the undergarment of the wearer.

Preferably the strips of adhesive 34 which attach the backsheet 26 to the undergarment of the wearer are provided in the geometry of two parallel lines symmetric about the longitudinal and lateral centerlines O—O and A—A. Preferably such adhesive strips do not lie along the longitudinal centerline O—O, so that the predisposition of the sanitary napkin 20 to assume the convex upward configuration of FIG. 3 is not inimically affected. Such adhesive may be provided in the geometry and configuration of commonly assigned International Publication No. WO 92/04000 published Mar. 19, 1992 in the name of Papa et al.

The topsheet 24 is compliant, soft feeling, and non-irritating to the wearer's skin. Further, the topsheet 24 is liquid pervious permitting liquids (e.g., menses and/or urine) to readily penetrate through its thickness. A suitable topsheet 24 may be manufactured from apertured formed films, foams, or woven and nonwoven materials comprised of natural or synthetic fibers. A preferred topsheet 24 comprises an apertured formed film as described in U.S. Pat. No. 3,929,135, entitled "Absorptive Structures Having Tapered Capillaries," which issued to Thompson on Dec. 30, 1975; U.S. Pat. No. 4,324,246 entitled "Disposable Absorbent Article Having A Stain Resistant Topsheet," which issued to Mullane, et al. on Apr. 13, 1982; U.S. Pat. No. 4,342,314 entitled "Resilient Plastic Web Exhibiting Fiber-Like Properties," which issued to Radel et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression," which issued to Ahr et al. on Jul. 31, 1984; and U.S. Pat. No. 5,006,394 entitled "Multilayer Polymeric Film," which issued to Baird on Apr. 9, 1991. Each of these patents is incorporated herein by reference. The preferred topsheet 24 for the present invention is the formed film described in one or more of the above patents and marketed by The Procter & Gamble Company of Cincinnati, Ohio as "DRI-WEAVE" for sanitary napkins 20. The backsheet 26 and the topsheet 24 are positioned adjacent the first and second major faces of the core 28 respectively, so that the core 28 is intermediate the backsheet 26 and topsheet 24. The backsheet 26 and topsheet 24 are preferably joined thereto and to each other by attachment means (not shown) such as are well known in the art. Adhesives which have been found to be satisfactory attachment means are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment," which issued to Minetola et al. on Mar. 4, 1986, and which is incorporated herein by reference. Alternative attachment means comprise heat, pressure, ultrasonic, and dynamic mechanical bonds.

In an alternative embodiment of the present invention, the sanitary napkin 20 has two flaps (not shown), each of which extend laterally beyond the longitudinal side margins of the sanitary napkin 20. The flaps are configured to drape over the edges of the wearer's undergarment. The flaps help prevent soiling by menstrual fluid, preferably by forming a double walled barrier along the edges of the undergarment. The flaps are preferably provided with attachment means on the garment surface, so that they can be folded back underneath the crotch of the undergarment. In this way the flaps serve to keep the sanitary napkin 20 properly positioned.

The flaps may be constructed of various materials including materials used for the topsheet 24, backsheet 26, combinations thereof, and may be a laminate having tissue in the center. Further, the flaps may be a separate element attached to the main body of the sanitary napkin 20 or can comprise extensions of the topsheet 24 and/or backsheet 26. Preferred flaps may be made in accordance with U.S. Pat. Nos. 4,589,876 issued May 20, 1986 to Van Tilburg or 4,687,478 issued Aug. 18, 1987 to Van Tilburg. Both of these patents are incorporated herein by reference.

The sanitary napkin 20 according to the present invention preferably has a crush resistance less than the 1.0 psi specified in the aforementioned U.S. Pat. No. 4,217,901 , issued to Bradstreet, which patent is incorporated herein by reference for the purpose of showing how to conduct a test for crush resistance. In order to clarify this test, the following conditions must be taken into account. The crush resistance test is formed by rolling the sanitary napkin 20 according to the present invention into a cylindrical configuration having the backsheet 26 facing outward. The cylinder is formed by abutting the ends of the absorbent core 28, or other components, of the sanitary napkin 20, as applicable, which contain the absorbent gelling materials 42. If the ends of the core 28 are not parallel to the lateral centerline A—A, the ends of the core 28 first to touch when abutted, while maintaining the longitudinal centerline O—O of the sanitary napkin 20 parallel to the longitudinal direction control the diameter of the cylinder.

If necessary, a small piece of tape, such as Scotch brand 810 tape, can be used to maintain the sanitary napkin 20 in the cylindrical configuration. The tape should be approximately one-half to three-quarters inches in width, one to one and one-half inches in length, be applied in the longitudinal direction along the longitudinal centerline O—O of the sanitary napkin 20 and be centered about the point where the ends of the core 28 abut.

The cylinder is placed in an Instron tensile machine having a load cell with a resolution of 1.0 grams. The cylinder is then crushed in the Instron machine at a crosshead speed of twenty inches per minute and the resulting load deflection curve recorded on a chart recorder having a chart speed of twenty inches per minute. If the sanitary napkin 20 does not remain upright for the test, a single probe or ruler may be used to stabilize the sanitary napkin 20 at its longitudinal edge, but only until it is fully engaged by the moving crosshead.

From the resulting load-deflection curve on the chart recorder, two values are found. The first value is the peak force in grams. The peak force corresponds to the point where the absorbent core 28 of the sanitary napkin 20, and hence the entire sanitary to napkin 20, buckles. Generally the peak force will be the highest force recorded before the sanitary napkin 20 starts to compress into a solid mass.

The second value is the last point of inflection the load-deflection curve demonstrates just before the aforementioned peak force. The inflection point is also measured in grams and may be found by any conventional computer program, spreadsheet program, or a chart recorder with a derivative function. In order to simplify the finding of the inflection point, the load-deflection curve may be directly input, as an analog voltage, to the computer and the inflection point found thereby.

The inflection point of the load-deflection curve, as used herein, is used consistent with the ordinary calculus definition, in occurring where the sense of concavity of the curve changes, and is found as the point where the second derivative of the curve is equal to zero. A more thorough discussion of inflection point, as used herein, is found in the reference book *The Calculus With Analytic Geometry* by Leithold, second edition, copyright 1972, Section 4.10 entitled "Concavity and Points of Inflection" beginning at page 227, which book is incorporated herein by reference. There are two crush resistances associated with the sanitary napkin 20, a peak crush resistance and an inflection point crush resistance. The crush resistance in either case is found by convening the appropriate reading, taken from either the peak or the inflection point in grams and convening it to pounds.

The area presented to the crosshead is computed. Such area is found by multiplying the length of the absorbent core 28 by the caliper of the entire sanitary napkin 20. If the absorbent core 28 is not uniform in the longitudinal direction, the greatest measurement taken parallel to the longitudinal centerline O—O is used.

The caliper of the sanitary napkin 20 is found by measuring a one inch diameter area of the sanitary napkin 20 under a confining pressure of 0.016 pounds per square inch. Such a light confining pressure is only believed suitable for finding caliper in the inflection point computation. Preferably the sanitary napkin 20 according to the present invention has a caliper, so measured, less than 3.5 millimeters, more preferably less than 3.3 millimeters, and most preferably less than 3.0 millimeters.

The reading in pounds is then divided by the area in square inches to yield the peak crush resistance or the inflection point crush resistance—depending upon which value was used in the numerator of the computation. One skilled in the art will understand that, based upon the above computation, as the caliper decreases, the apparent crush resistance will increase. The sanitary napkin 20 according to the present invention preferably has a peak crush resistance less than 0.6 psi and more preferably less than 0.5 psi. The sanitary napkin 20 according to the present invention also preferably has an inflection point crush resistance less than 0.5 psi and more preferably less than 0.4 psi.

While it will be apparent that many other configurations, combinations, and permutations of the foregoing are feasible, all such variations fall within the scope of the appended claims.

What is claimed is:

1. A sanitary napkin comprising:

a liquid pervious topsheet;

a liquid impervious backsheet joined to said topsheet; and an absorbent core further comprising absorbent gelling material, said core being intermediate said topsheet and said backsheet;

said sanitary napkin having a peak crush resistance less than 0.6 psi.

2. A sanitary napkin according to claim 1 wherein said peak crush resistance is less than 0.5 psi.

3. A sanitary napkin according to claim 1 having a caliper of less than 3.5 millimeters.

4. A sanitary napkin according to claim 3 having a caliper of less than 3.0 millimeters.

5. A sanitary napkin comprising:

a liquid pervious top sheet;

a liquid impervious backsheet joined to said topsheet; and an absorbent core further comprising absorbent gelling material, said core being intermediate said topsheet and said backsheet;

said sanitary napkin having an inflection point crush resistance less than 0.5 psi.

6. A sanitary napkin according to claim 5 wherein said inflection point crush resistance is less than 0.4 psi.

7. A sanitary napkin according to claim 5 having a caliper of less than 3.5 millimeters.

8. A sanitary napkin according to claim 7 having a caliper of less than 3.0 millimeters.

\* \* \* \* \*

UNITED STATES PATENT AND TRADEMARK OFFICE
CERTIFICATE OF CORRECTION

PATENT NO. : 5,569,231
DATED : October 29, 1996
INVENTOR(S) : Ralph R. Emenaker et al.

It is certified that error appears in the above-indentified patent and that said Letters Patent is hereby corrected as shown below:

Column 2, line 40     delete "told" and insert --fold--.

Column 11, line 22     delete "to".

Column 11, lines 47, 48   delete "convening" and insert therefor --converting--.

Signed and Sealed this

Fifteenth Day of April, 1997

*Attest:*

BRUCE LEHMAN

*Attesting Officer*     *Commissioner of Patents and Trademarks*